United States Patent [19]

Stobaugh et al.

[11] Patent Number: 4,891,323

[45] Date of Patent: Jan. 2, 1990

[54] METHOD FOR ASSAYING PRIMARY AMINES, SECONDARY AMINES AND PEPTIDES USING FLUOROGENIC DERIVATIZATION REAGENTS

[75] Inventors: John F. Stobaugh; Sunil Kakodkar, both of Lawrence, Kans.

[73] Assignee: Oread Laboratories, Inc., Lawrence, Kans.

[21] Appl. No.: 24,479

[22] Filed: Mar. 11, 1987

[51] Int. Cl.$^4$ ................. G01N 21/77; G01N 33/68
[52] U.S. Cl. .......................... 436/86; 436/89; 436/90; 436/111; 436/172
[58] Field of Search ............ 436/86, 87, 88, 89, 436/90, 111, 161, 172

[56] References Cited

U.S. PATENT DOCUMENTS

| | | | |
|---|---|---|---|
| 4,359,323 | 11/1982 | LePage | 436/89 |
| 4,419,452 | 12/1983 | Imai et al. | 436/89 |
| 4,670,403 | 6/1987 | Ishida et al. | 436/89 X |
| 4,758,520 | 7/1988 | Matuszewski et al. | 436/86 |

FOREIGN PATENT DOCUMENTS 0233973  9/1987  European Pat. Off. ............ 436/89

OTHER PUBLICATIONS

Gardner et al, Anal. Biochem, vol. 101, pp. 61–65, 1980.

Larsen et al, J. of Chromatographic Science, vol. 19, pp. 259–265, 1981.

Ishida et al, J. of Chromatography, vol. 204, pp. 143–148, 1981.

Kucera et al, J. of Chromatography, vol. 255, pp. 563–579, 1983.

Primary Examiner—Robert J. Hill, Jr.
Attorney, Agent, or Firm—Burns, Doane, Swecker & Mathis

[57] ABSTRACT

Primary amines, secondary amines and peptides are fluorometrically assayed using a fluorogenic derivatization reagent of the formula:

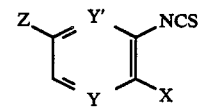

where Z is an electron withdrawing group or a fused benzene ring, Y and Y', which are identical or different, are nitrogen or carbon and X is a halogen or other leaving group. The above fluorogenic reagent reacts with the primary amine, secondary amine or peptide to form a cyclic fluorescent adduct.

7 Claims, 1 Drawing Sheet

METHOD FOR ASSAYING PRIMARY AMINES, SECONDARY AMINES AND PEPTIDES USING FLUOROGENIC DERIVATIZATION REAGENTS

BACKGROUND OF THE INVENTION

The present invention relates to assaying compounds containing primary and secondary amino groups and more particularly to novel compounds which react with primary or secondary amines to form adducts amenable to fluorometric detection techniques.

The biological role of peptides, either of endogenous or exogenous origin, is of great interest to researchers. This interest has been particularly evident ever since the discovery of the body's natural opioid peptides including $\beta$-endorphin, Met-enkephalin and Leu-enkephalin. Interest has also been enhanced by the discovery that endogenous peptides take part in many varied biological processes, including regulation of blood pressure and neurotransmission, which is regulated by peptides such as atrial natriuretic factor and neuropeptide. Such discoveries, coupled with recent advances in biotechnology, have led to the active investigation by many pharmaceutical companies of the possibility of developing drugs based on naturally occurring peptides or their synthetic analogs.

Of course, the study of the biological role of various peptides for possible future pharmaceutical applications requires techniques enabling isolation and precise quantification of such peptides in biological fluids and tissues of interest. Isolation, or selectivity, involves utilization of a technique for separating a given peptide from other peptides as well as from other biological compounds. In recent years, the technique of high performance liquid chromatography (HPLC) has emerged as the dominant technique available for fractionating complex biological samples and providing the required selectivity. Quantification involves determining the amount of the isolated peptide present in a biological sample.

Unfortunately, amino acids and peptides present in biological fluids do not possess the physical properties necessary to allow their quantification at their naturally occurring concentration levels, i.e., at concentrations of $10^{-9}$ mole/liter (nanomoles/liter) or less. One frequently employed approach to overcome this problem is to chemically modify (derivatize) the peptide or amino acid, such as by fluorescent labelling, prior to or after isolating the various peptides or amino acids by HPLC. In peptide and amino acid analysis, the chemical handle most amenable to chemical derivatization is the primary or secondary amino group of the N-terminus for a peptide or the $\alpha$-amino group for any amino acid.

Several properties should be possessed by a derivatization agent used to fluorescently label peptides or amino acids. First, the derivatization reagent should be capable of reacting with both primary and secondary amines. Secondly, the reagent should be fluorogenic, i.e., not itself fluorescent but capable of forming a fluorescent adduct upon reaction with the peptide or amino acid. Thirdly, the reagent should be capable of forming a chemically stable adduct with a primary or secondary amine. Fourthly, the adduct formed should exhibit a high fluorescence efficiency in the aqueous/organic solvent systems utilized in HPLC. Finally, the reagent should react with the primary or secondary amine compound under relatively mild reaction conditions.

Over the years, a number of fluorogenic derivatization reagents for amines have been developed. For example, ortho-phthalaldehyde (OPA) and fluorescamine have been employed for the fluorogenic derivatization of primary amines. However, such compounds do not form fluorescent derivatives with secondary amines. Additionally, OPA only forms fluorescent derivatives with amino acids and not peptides whereas fluorescamine forms two products with amino acids. Other fluorogenic derivatization reagents for amines include dansyl-chloride (Dans-Cl) and 4-chloro(fluoro)-7-nitrobenzo-2-oxa-1,3-diazole [NBD-Cl(F)]. However, Dans-Cl usually does not react to give quantitative yields. Additionally, excess Dans-Cl forms a hydrolysis product, Dans-OH, which has the potential for interfering with the dansylated amines. NBD-Cl and NBD-F amine derivatives exhibit substantially compromised fluorescence quantum efficiencies in media containing a large fraction of water which, unfortunately, is commonly encountered in HPLC.

SUMMARY AND OBJECTS OF THE INVENTION

In view of the foregoing limitations and shortcomings of prior art fluorogenic derivatization reagents as well as other disadvantages not specifically mentioned above, it should be apparent that there still exists a need in the art for a fluorogenic derivatization reagent enabling quantification of minute amounts of primary amines, secondary amines and peptides in a sample. It is, therefore, a primary objective of this invention to fulfill that need by providing new fluorogenic derivatization agents, a method of fluorometrically assaying primary amines, secondary amines and peptides using the new fluorogenic derivatization agents and fluorescent adducts formed by reacting the new fluorogenic derivatization reagents with primary amines, secondary amines and peptides.

More particularly, it is an object of this invention to provide fluorogenic derivatization reagents which enable quantification of primary amines, secondary amines and peptides at naturally occurring concentration levels, i.e., at nanomolar levels and below.

It is a further object of this invention to provide fluorogenic derivatization reagents which form chemically stable adducts with the above amine compounds.

Yet another object of this invention is to provide fluorogenic derivatization reagents forming adducts with the above amine compounds which exhibit a high fluorescence efficiency in the aqueous/organic solvent systems utilized in HPLC.

Still another object of this invention is to provide fluorogenic derivatization reagents which form adducts with the above amine compounds under relatively mild reaction conditions to produce a single product in quantitative yield.

Briefly described, these and other objects of the invention are accomplished by providing fluorogenic derivatization reagents of the formula:

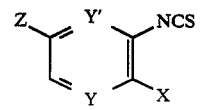

wherein Z is an electron withdrawing group or a fused benzene ring, Y and Y', which are identical or different, are nitrogen or carbon and X is a halogen or other leaving group.

In another aspect, the invention relates to a method of fluorometrically assaying a primary amine, secondary amine or peptide comprising the steps of:

(i) coupling an isothiocyanate with the primary amine, secondary amine or peptide to form a thiourea as follows:

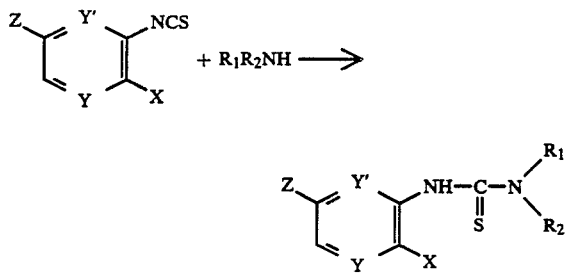

wherein Z is an electron withdrawing group or a fused benzene ring, Y and Y', which are identical or different, are nitrogen or carbon and X is a halogen or other leaving group, $R_1$ is H or an alkyl and $R_2$ is an alkyl or a peptide residue;

(ii) cyclizing the thiourea into a product exhibiting fluorescence as follows:

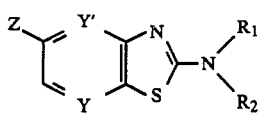

(iii) assaying the product exhibiting fluorescence.

In yet another aspect, the invention relates to fluorescent adducts of the formula:

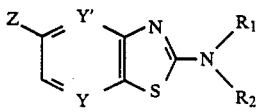

wherein Z is an electron withdrawing group or a fused benzene ring, Y and Y', which are identical or different, are nitrogen or carbon, X is a halogen or other leaving group, $R_1$ is H or an alkyl group and $R_2$ is an alkyl group or a peptide residue.

With the foregoing and other objects, advantages, and features of the invention that will become hereinafter apparent, the nature of the invention will be more clearly understood by reference to the following detailed description of the invention, the appended claims and the drawings.

DETAILED DESCRIPTION OF PREFERRED EMBODIMENTS

Figure 1A:
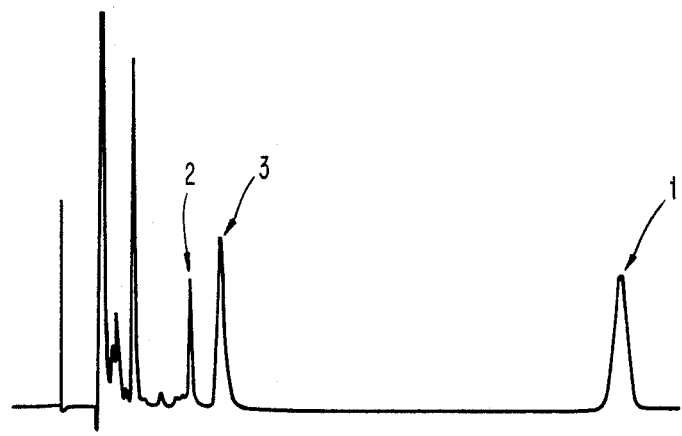
FIGS. 1a and 1b are chromatograms depicting cyclization of the product formed by the coupling reaction of 3-isothiocyano-2-chloro-pyridine and isopropylamine.

The fluorogenic derivatization reagents of the present invention are of the formula:

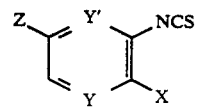

wherein Z is an electron withdrawing group or a fused benzene ring, Y and Y', which are identical or different, are nitrogen or carbon and X is a halogen or other leaving group.

Z is an electron withdrawing group. For purposes of the present invention, electron withdrawing groups include hydrogen and atoms or groups of atoms that have electron-withdrawing inductive effects which are more electronegative than is hydrogen. Exemplary electron withdrawing groups Z are H, I, Br, Cl, F, $CO_2H$, $NO_2$, OH, $OCH_3$,

a fused benzene ring or a ring formed from a methylene dioxy group·

It is also possible to provide two adjacent electron withdrawing groups at Z and its adjacent carbon. For example, there may be used a compound of the formula:

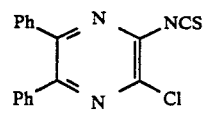

X is a good leaving group such as a halogen. Of course, persons skilled in the art will appreciate that while halogens are the most commonly employed leaving groups, other leaving groups, which may be readily ascertained by persons skilled in the art, are contemplated. Although X is located on the ring between the isothiocyanate group and Y', it is also possible to locate the substituent X at Y' when Y' is carbon.

Preferred among the fluorogenic derivatization reagents falling within the above definition are compounds of the formulae:

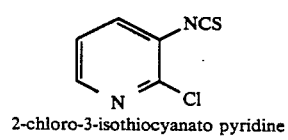

2-chloro-3-isothiocyanato pyridine

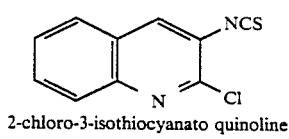

2-chloro-3-isothiocyanato quinoline

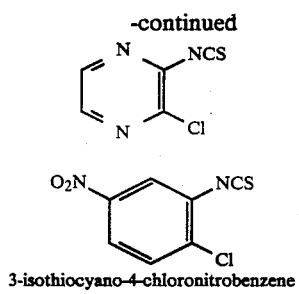

3-isothiocyano-4-chloronitrobenzene

PREPARATION OF 2-CHLORO-b 3-ISOTHIOCYANATO PYRIDINE (I)

Compound (I) namely, 2-chloro-3-isothiocyanato pyridine was prepared by reacting 2-chloro-3-amino pyridine and thiophosgene as follows:

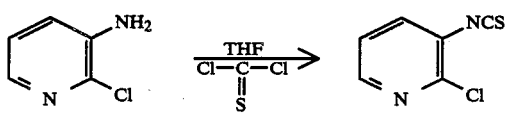

0.5 g (0.0039 mol) of 2-chloro-3-amino pyridine was dissolved in 30 ml of freshly distilled tetrahydrofuran (THF) in a three-necked 100 ml round bottom flask fitted with a nitrogen inlet. 0.86 ml (0.0113 mol) of thiophosgene was quickly added in one portion from a syringe and the mixture was stirred at room temperature for one-half hour. Analysis by thin layer chromatography (TLC) (silica gel/hexane/isopropanol 8:2) showed the absence of starting materials. The THF was evaporated on a rotary film evaporator and the residue was dissolved in 50 ml of dichloromethane, washed twice with 50 ml water, once with 50 ml of saturated sodium chloride, dried over sodium sulfate and evaporated to give an oily isothiocyanate product with solidified while stored overnight in a refrigerator. The isothiocyanate product was purified by sublimation to give light yellow crystals which were low melting and which underwent liquification at room temperature. The crystals were stored under $N_2$ in a freezer and were protected from light. The compound had to be used immediately for derivatization since it was unstable.

PREPARATION OF 3-ISOTHIOCYANO-4-CHLORO-NITROBENZENE (IV)

Compound (IV) namely, 3-isothiocyano-4-chloronitrobenzene was prepared by reacting 2-chloro-5-nitro-aniline and thiophosgene as follows:

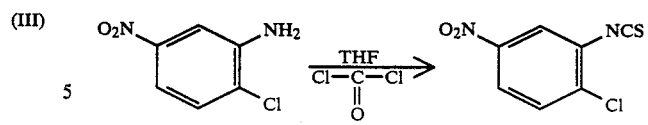

1.725 g (0.01 mol) of 2-chloro-5-nitro-aniline was added to a 100 ml 3-necked flask fitted with a condenser, a nitrogen inlet and a magnetic stirrer. The compound was dissolved in 25 ml of freshly distilled dry THF. 3.42 g (0.03 mol) of thiophosgene was quickly added in one portion from a syringe and the mixture was refluxed for 30–45 minutes. TLC analysis (silica gel/$CH_2Cl_2$) showed the absence of starting material. The solution was evaporated, and the residue was dissolved in dichloromethane, washed twice with 50 ml water, once with 50 ml of saturated sodium chloride, dried with sodium sulfate and evaporated on a rotary film evaporator to give an oily product which solidified on cooling. The 3-isothiocyano-4-chloro-nitrobenzene product (IV) was purified by column chromatography on silica gel using $CH_2Cl_2$ as the eluting solvent ($M^+$ 214). The product was unstable at room temperature and therefore was used immediately in subsequent reactions.

PREPARATION OF 2-CHLORO-3-ISOTHIOCYANATO QUINOLINE

Compound (IV) namely, 2-chloro-3-isothiocyanato quinoline is prepared by the following reaction scheme:

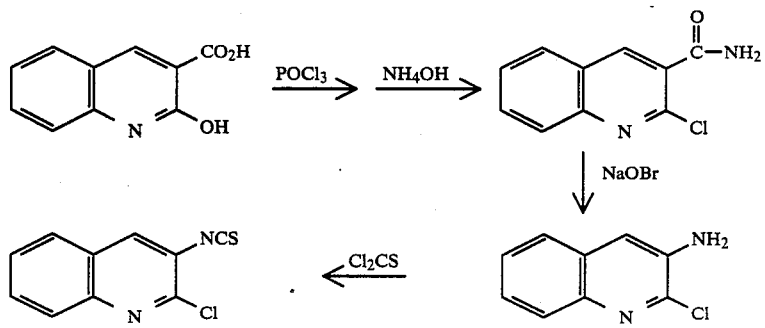

The fluorogenic derivatization reagents described above are reacted with primary amines, secondary amines or peptides of the formula $R_1R_2NH$. In the case of primary amines, $R_1$ is hydrogen and $R_2$ is an alkyl group such as a $C_1$–$C_8$ alkyl. In the case of secondary amines, $R_1$ and $R_2$ are both alkyl groups such as $C_1$–$C_8$ alkyls. Alternatively, $R_1$ and $R_2$ could form a cyclic secondary amine. In the case of peptides, $R_1$ is generally hydrogen and $R_2$ is a peptide residue. By peptide residue is meant the peptide compound excluding the —$NH_2$ function. Thus, in a peptide formed from two amino acids of the formula:

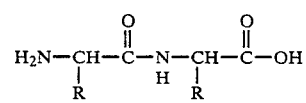

the peptide residue is:

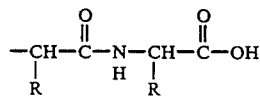

The substituents R in the above formulae, of course, depend on which amino acids were employed as the peptide precursors. The present derivitization technique is generally applicable to polypeptides.

The primary amines, secondary amines and/or peptides are coupled with the aforedescribed fluorogenic derivatization reagents as follows:

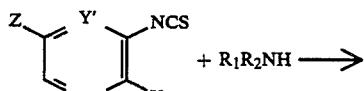

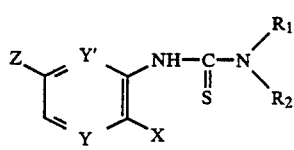

The reaction may be carried out in a solvent such as THF at room temperature.

The thiourea compound is then converted to a cyclized product by a cyclization reaction as follows:

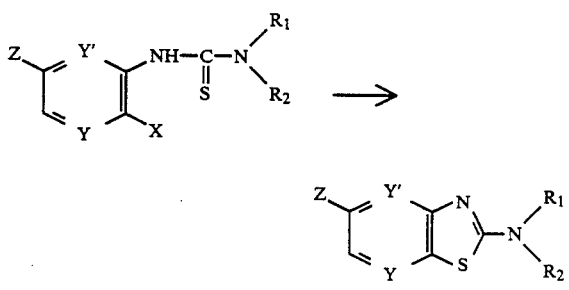

The above cyclization reaction is possible since the ortho-substituent (X) on the ring is activated since (1) X is a halogen or other good leaving group, (2) Y and Y' are nitrogen or carbon and (3) Z is an electron withdrawing group or a fused benzene ring. By virtue of this activation, the nucleophilic thiourea produced by the coupling reaction directs its attack towards the ortho substituent X rather than the peptide bond thereby forming a fused ring system product exhibiting fluorescence.

The cyclization reaction may be carried out by dissolving the thiourea compound in dry dimethylformamide (DMF) to form a solution containing $10^{-5}$ to $10^{-3}$M of the thiourea, adding $10^{-4}$ to $10^{-2}$M of tetramethylguanidine (TMG), heating between 60° and 70° C. for about 30 minutes and, after confirming absence of starting material by TLC, quenching with water. The cyclization may also be carried out in aqueous solutions. In such instances, however, it is generally necessary to add a small amount of an acid such as HCl.

COUPLING AND CYCLIZATION OF 3-ISOTHIOCYANO-4-CHLORO-NITROBENZENE AND ISOPROPYLAMINE 3-isothiocyano-4-chloro-nitrobenzene was coupled with isopropylamine to form a thiourea as follows:

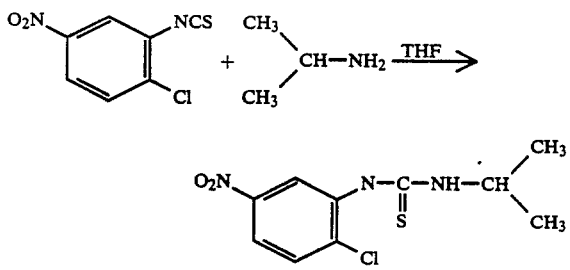

1.8 g (0.008 mol) of 3-isothiocyano-4-chloro-nitrobenzene was dissolved in 25 ml of freshly distilled dry THF in a 100 ml 3-necked round bottom flask fitted with a condenser, a nitrogen inlet and a magnetic stirrer. 0.546 g. (0.009 mol) of isopropylamine was quickly added by means of a syringe and the mixture was stirred at room temperature for 30–45 minutes. TLC analysis (silica gel, hexane/EtoAC 1:1) showed absence of starting materials and formation of a new product. The solution was evaporated to give a solid thiourea product. It was crystallized from hexane/ethyl acetate to give crystalline needles. m.p. 147°–149° C., (1.16 g, 51%) [M+, 273 E.I.] [M+$^1$274$^{C.I.}$]

The resulting thiourea was then cyclized as follows:

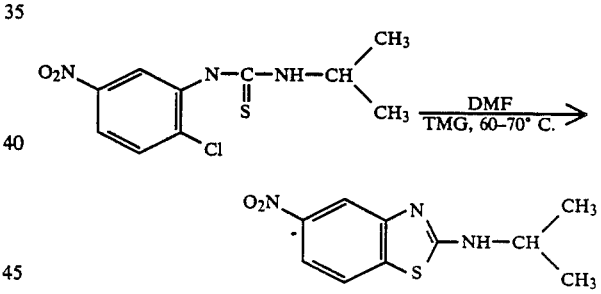

1.0 g (0.003 mol) of the above thiourea was dissolved in 5 ml of dry DMF (gold label, Aldrich Chemical Co.) in a 25 ml 3-neck flask fitted with a condenser, a nitrogen inlet, a magnetic stirrer and a heating mantle. To this solution, 1 ml (0.0073 mol) tetramethyl guanidine (TMG) was added by means of a syringe. The solution was heated between 60°–70° C. for 30 minutes at which time TLC analysis (silica gel, hexane/EtoAc 1:1) showed the absence of starting material. The reaction was quenched with 7 ml of water and a yellow benzthiazole cyclization product was collected by filtration. It was crystallized from benzene/hexane to give bright yellow needles. m.p. 174°–176° C. (0.6 g, 69.7%) [M$^{31}$ 237 E.I.]

COUPLING AND CYCLIZATION OF 3-ISOTHIOCYANO-2-CHLORO-PYRIDINE AND ISOPROPYLAMINE 3-isothiocyano-2-chloro-pyridine was coupled with isopropylamine to form a thiourea which cyclized into a pyridine-thiazole product as follows:

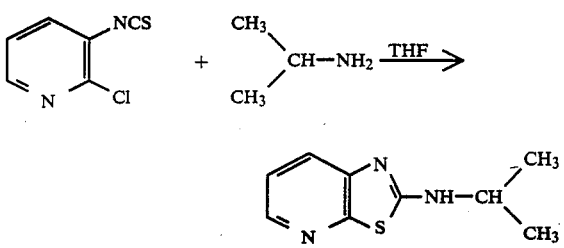

0.7 g (0.0044 mol) of 3-isothiocyano-2-chloro-pyridine was dissolved in 25 ml of freshly distilled dry THF in a 100 ml 3-necked flask fitted with a magnetic stirrer, a condenser and a nitrogen inlet. 0.29 g (0.005 mol) of isopropylamine was quickly added by means of a syringe and the mixture was stirred at room temperature for 30–45 minutes. TLC analysis (silica gel, hexane/isopropanol 8:2) showed absence of starting material and the formation of a new cyclized product. The solvent was evaporated on a rotary film evaporator and the red oil was chromatographed on silica gel/hexane:isopropanol 8:2. Fractions were collected and the fractions corresponding to the new cyclized product were combined and evaporated to give yellow oil which solidified when kept under high vacuum overnight. It was further recrystallized from (benzene:hexane) to give yellow crystalline needles (0.5 g, 73–5%) m.p. 126°–128° C. $E_{232}=17517M^{-1}cm^{-1}$, $E_{268}=13227M^{-1}cm^{-1}$, $E_{300}=8324M^{-1}cm^{-1}$. $M^+$ Cal. for $C_9H_{11}N_3S=193.0673$ Peak match (observed) 193.0670.

The above reaction was carried out in an aqueous acetonitrile reaction medium. 1.09 μM 3-isothiocyano-2-chloro-pyridine was coupled with 0.058 μM of isopropylamine in a reaction medium containing 80% acetonitrile. The materials were heated to 70° C. for 60 minutes and allowed to stand overnight. Upon addition of 2 drops of concentrated HCl, which lowered the pH from 7.2 to 0.95, the cyclized product formed.

The progress of the above reaction sequence was followed by HPLC. The conditions under which the HPLC was performed were as follows:
Mobile Phase 30% Acetonitrile+70% Phosphate Buffer PH=3
Flow Rate 1.5 ml./min.
Abs. 1.00, 254 nm
Chart Speed 0.2"/min.
Injection Vol. 50 μl.
2-Chloro-3-Amino-Pyridine 2.5 min.
2-Chloro-3-Isothiocyano-Pyridine 19.5 min.[1]
Intermediate 4.25 min.[2]
Cyclized Product 5.4 min.[3]

Figure 1B:
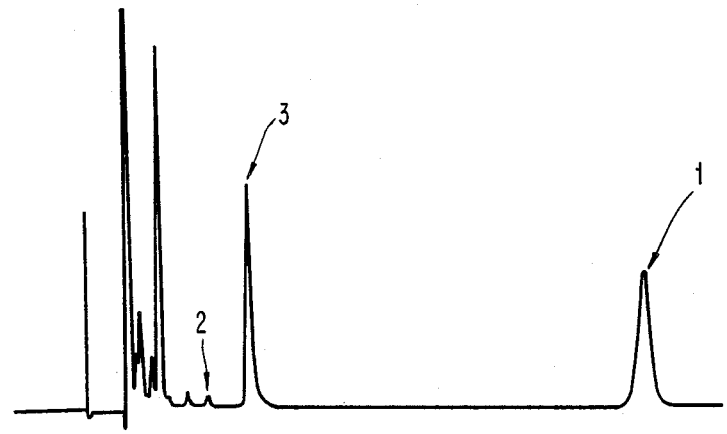

The conversion of the thiourea coupling product to the cyclized product is demonstrated in FIGS. 1a and 1b which depict chromatograms taken of the system after one hour (FIGS. 1a) and after 2 hours (FIG. 1b). The peak 1 depicts 3-isothiocyano-2-chloro-pyridine. The peak 2 depicts the coupling product of 3-isothiocyano-2-chloro-pyridine with isopropylamine and the peak 3 depicts the cyclization product. As is evident from the chromatogram, the peak 2 (coupling product) dimishes with time as the peak 3 (cyclization product) emerges.

COUPLING AND CYCLIZATION OF 3-ISOTHIOCYANO-2-CHLORO-PYRIDINE AND N-METHYLBUTYLAMINE (SECONDARY AMINE)

3-isothiocyano-2-chloro-pyridine was coupled with n-methylbutylamine to form a thiourea which cyclized into a pyridine-thiazole product as follows

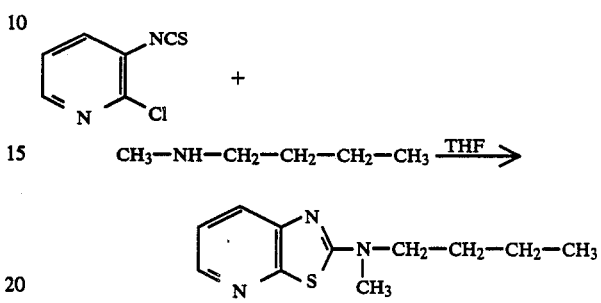

1.8 g (0.01 mol) of 3-isothiocyano-2-chloro-pyridine were dissolved in 50 ml of freshly distilled anhydrous THF in a 100 ml 3-necked flask fitted with a magnetic stirrer, nitrogen inlet and a condenser. 1.01 g (0.0116 mol) of n-methylbutylamine was added quickly by means of a syringe and the mixture was stirred at room temperature for 30 minutes after which TLC (silica gel, hexane/isopropanol 8:2) showed the absence of starting materials. The solvent was evaporated on a rotary film evaporator and the oil thus obtained was purified by column chromatography (silica gel, hexane/isopropanol 8:2). The yellow oil obtained failed to crystallize. ($M^+$,221)

FLUORESCENCE CHARACTERISTICS

The quantum yield in various solvents was determined for the cyclization product:

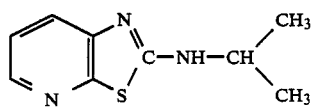

The results of that determination are as follows:

TABLE

| QUANTUM YIELD | |
|---|---|
| | RELATIVE QUANTUM YIELD |
| (1) 1N HCl | 0.58 |
| (2) 0.1N HCl | 0.09 |
| (3) PHOSPHATE BUFFER PH = 3 | 0.016 |
| (4) ACETATE BUFFER PH = 5 | 0.01 |
| (5) PHOSPHATE BUFFER PH = 7 | 0.024 |
| (6) BORATE BUFFER PH = 9.2 | 0.044 |
| (7) PHOSPHATE BUFFER PH = 12 | 0.046 |
| (8) 1N NAOH | — |
| (9) ACETONITRILE | |

The emission wavelength was 360 nm and the excitation wavelength was 300 nm. As is evident from the above Table, an excellent fluorescence yield is obtained in a 1N HCl solution.

When assaying a sample containing a plurality of primary amines, secondary amines or peptides, it is desirable to separate the various analytes from one another by a technique having high selectivity such as HPLC. The HPLC may be performed either before or after reacting the amines with the fluorogenic derivatization reagents. Such techniques are well known to persons skilled in the art.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method of fluorometrically assaying primary amines, secondary amines or peptides in a sample comprising the steps of:

(i) contacting a sample containing a primary amine, a secondary amine, or a peptide with an isothiocyanate so that the isothiocyanate couples with the primary amine, secondary amine or peptide in the sample to form a thiourea as follows:

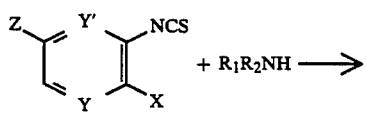 + $R_1R_2NH \longrightarrow$

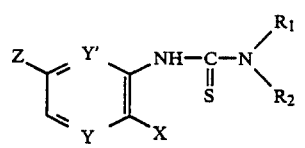

wherein Z is an electron withdrawing group or a fused benzene ring, Y and Y', which are identical or different, are nitrogen or carbon and X is a halogen or other leaving group, $R_1$ is H or an alkyl and $R_2$ is an alkyl or a peptide residue;

(ii) cyclizing the thiourea into a cyclization product exhibiting fluorescence as follows:

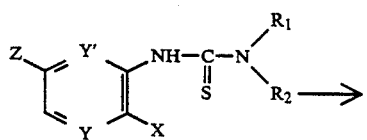

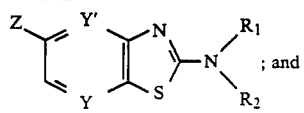

(iii) fluorometrically assaying the product exhibiting fluorescence.

2. The method of claim 1 wherein said isothiocyanate is of the formula:

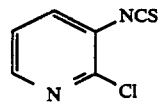

3. The method of claim 1 wherein said isothiocyanate is of the formula:

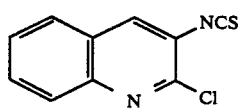

4. The method of claim 1 wherein said isothiocyanate is of the formula:

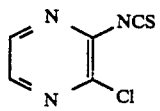

5. The method of claim 1 wherein said isothiocyanate is of the formula:

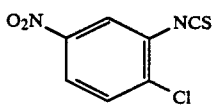

6. The method of claim 1 wherein the sample contains a plurality of primary amines, secondary amines or peptides which are assayed and wherein the method further comprises separating said plurality of primary amines, secondary amines, or peptides by high performance liquid chromatography before step (i).

7. The method of claim 1 wherein the sample contains a plurality of primary amines, secondary amines or peptides which are assayed, wherein a plurality of cyclization products are produced in step (ii), and wherein the method further comprises separating said plurality of cyclization products by high performance liquid chromatography before step (iii).

* * * * *